United States Patent [19]

Benziman et al.

[11] Patent Number: 5,382,656

[45] Date of Patent: Jan. 17, 1995

[54] CELLULOSE SYNTHASE ASSOCIATED PROTEINS

[75] Inventors: Moshe Benziman, Jerusalem, Israel; Rony Tal, Coral Springs, Fla.

[73] Assignee: Weyerhaeuser Company, Federal Way, Wash.

[21] Appl. No.: 958,042

[22] Filed: Oct. 6, 1992

[51] Int. Cl.6 .................... C07K 15/04; C12N 9/12
[52] U.S. Cl. .................... 530/350; 435/194; 435/823
[58] Field of Search .................... 530/350, 370

[56] References Cited

FOREIGN PATENT DOCUMENTS 0260093 3/1988 European Pat. Off. .
WO90/12098 10/1990 WIPO .

OTHER PUBLICATIONS

Lin, F. C., et al., in *Proceedings of the Tenth Cellulose Conference*, p. 27, Jun. 1988.
Saxena, I. M., et al., Plant Molecular Biology, vol. 15, No. 5, pp. 673–683, Nov., 1990.
Saxena, I. M. et al., Plant Molecular Biology, vol. 16, No. 6, pp. 947–954, Jun., 1991.
Cannon, R. E., et al., Microbiology 1991, pp. 435–447, 1991.
Mayer, et al., "Polypeptide composition of bacterial cyclis diguanylic acid–dependent cellulose synthase and the occurrence of immunologically crossreacting proteins in higher plants", *Proc. Natl. Acad. Sci. USA* 88: 5472–5476 (1991).
Lin & Brown, "Purification of Cellulose Synthase from *Acetobacter Xylinum*", *Cellulose and Wood*, Conrad Schuerch, Editor, Wiley, N.Y. pp. 473–492 (1989).
Wong, et al., "Genetic organization of the cellulose synthase operon in *Acetobacter xylinum*", *Proc. Natl. Acad. Sci. USA* 87: 8130–8134 (1990).
Ross, et al., "Cellulose Biosynthesis and Function in Bacteria", *Microbiological Reviews* 55: 35–58 (1991).

Primary Examiner—Robert A. Wax
Assistant Examiner—William W. Moore
Attorney, Agent, or Firm—Pennie & Edmonds

[57] ABSTRACT

Novel proteins capable of binding to bacterial cellulose synthase are provided. Proteins that co-purify with bacterial cellulose synthase and have approximate relative molecular weights of 20 kDa, 54 kDa and 59 kDa are taught. Also provided for are nucleotide sequences encoding the proteins, antibodies to the proteins, and recombinant host cells for the expression of the cellulose synthase associated (co-purifying) proteins. The cellulose synthase associated proteins (CSAPs) CSAP20 (SEQ ID NO: 1) CSAP54 (SEQ ID NO: 2), and CSAP59 (SEQ ID NO: 3) are specifically provided for.

5 Claims, No Drawings 5,382,656

CELLULOSE SYNTHASE ASSOCIATED PROTEINS

TECHNICAL FIELD OF THE INVENTION

The invention relates to the field of proteins and genes encoding proteins. More specifically, the invention relates to proteins that co-purify with the cellulose synthase complex.

BACKGROUND OF THE INVENTION

Cellulose is relied upon as the raw material for a number of useful products including paper products and wound dressings. Cellulose may be obtained from plants and various microorganisms in culture, for example from the cellulose producing bacteria of the genus Acetobacter. Acetobacter is characteristically a Gram-negative, rod-shaped bacterium 0.6–0.8 μm by 1.0–4 μm. The organism is strictly aerobic; metabolism is respiratory, never fermentative. It is further distinguished by the ability to produce multiple poly β(1-4)-glucan chains, chemically identical to cellulose. Multiple cellulose chains or microfibrils are synthesized at the bacterial surface at sites on the cell wall. The production of cellulose by Acetobacter has been the subject of intense study since at least the 1930's. In particular, *Acetobacter xylinum* has been widely studied to attempt to elucidate the mechanism of cellulose synthesis in intact cells [Schramm and Hestrin, (1954) *J. Gen. Microbiol.* 11:123–129].

The enzymatic pathway for cellulose synthesis in *Acetobacter xylinum* has been investigated and essentially four enzymatic steps have been characterized in cell-free extracts of *A. xylinum* which appear to comprise the complete pathway from glucose to cellulose. These are the phosphorylation of glucose by glucokinase [Benziman, et al., (1972) *J. Bacteriol.*, 111:325–330], the isomerization of glucose-6-phosphate to glucose-1-phosphate by phosphoglucomutase [Gromet, et al., (1957) Biochem. J., 67:67914 689; Frei-Roitman, Factors affecting the activity of phosphoglucomutase and UDP-glucose pyrophosphorylase of *Acetobacter xylinum*, M.Sc. thesis, The Hebrew University of Jerusalem, Jerusalem, Israel (1974)]; the synthesis of uridine 5'-diphosphoglucose (UDP-glc) by UDPG-pyrophosphorylase, [Frei-Roitman, supra; Swissa, Biosynthesis of cellulose in *Acetobacter xylinum*, Ph.D. thesis, The Hebrew University of Jerusalem, Jerusalem, Israel (1978)], and the cellulose synthase reaction.

A detailed review of the genetics and biochemistry of cellulose synthesis in Acetobacter and other cellulose producing bacteria is provided in Ross, et al., *Microbiological Reviews*, 55:35–38 (1991).

Early attempts to purify cellulose synthase from a strain of *A. xylinum* employing conventional chromatographic techniques have not been especially successful, but recently the enzyme has been significantly purified and its properties and structure in the purified state have been investigated (Mayer et al., *Proc. Natl. Acad. Sci. USA* 88:5472–5476 (1991)).

Similarly, attempts to purify cellulose synthase by in vitro cellulose entrapment and chromatographic techniques have resulted in a partially purified 83 kilodalton (kD) polypeptide (Lin and Brown, in Cellulose and Wood-Chemistry and Technology (1989) ED. Scharch, Wiley, N.Y. pp.473–492).

A more complete knowledge of the biochemistry of cellulose synthesis would facilitate greater productivity and yield of cellulose from cultures of cellulose-producing microorganisms.

The formation of cellulose, i.e., the polymerization of glucose, appears to be catalyzed by the gene product of the bcsA gene product of the bcs (bacterial cellulose synthase operon). The bcsA gene product appears to be physically associated with a regulatory subunit that is the product of the bcsB gene. Mutations in the other bcs operon genes have shown that these genes are also important for cellulose synthesis, as described in Wong et al. *Proc. Natl. Acad. Sci.* 87:8130–8134 (1990).

In addition to the bcsA, bcsB, bcsC and bcsD gene products of the bcs operon, several other proteins may be involved in the production of cellulose in vivo. The identification of these additional proteins may be useful in regulating cellulose production by recombinant micro-organisms because, among other reason, altering the expressive level of these proteins in cellulose producing bacteria may be used to modulate the production of cellulose. Some of these proteins may physically interact with cellulose synthase. Those proteins capable of interacting with cellulose synthase have a variety of uses in addition to their biological activity. These biological activity independent uses of cellulose synthase interacting proteins are based, at least in part, on the specific interaction between the cellulose synthase interacting proteins and cellulose synthase.

SUMMARY OF THE INVENTION

The present invention provides for three novel proteins, CSAP20, (SEQ ID NO: 1) CSAP 54 (SEQ ID NO: 2) and CSAP59 (SEQ ID NO: 3) thereof), in purified form. Similarly, the subject invention provides nucleotide sequences encoding these proteins, namely, genes csap20, csap54 and csap59, and fragments thereof. Another aspect of the present invention is to provide for the recombinant production of the subject proteins and to provide host cells for the production of these proteins. An additional aspect of the invention is to provide for strains of various microorganisms that naturally produce CSAP proteins, but are genetically modified so as to produce one or more of the CSAP proteins in altered amounts. The present invention also provides for antibodies (or similar specific binding molecules) specific for individual CSAP proteins.

DESCRIPTION OF THE SPECIFIC EMBODIMENTS

CSAP (Cellulose Synthase Associated Proteins) are proteins that co-purify with cellulose synthase. Three novel CSAP proteins have been specifically identified by the inventors, namely, CSAP20, (SEQ ID NO: 1) CSAP54 (SEQ ID NO: 2) and CSAP59 (SEQ ID NO: 3). The term CSAP includes CSAP20 (SEQ IN NO: 1), CSAP54 (SEQ ID NO: 2) and CSAP59 (SEQ ID NO: 3). The CSAP proteins were identified in the process of purifying *Acetobacter xylinum* cellulose synthase by cellulose synthase entrapment. Analysis of the proteins co-purifying with cellulose synthase has resulted in the identification of three novel proteins that are not encoded by cellulose synthase operon genes bcsA, bcsB, bcsC or bcsD.

CSAP20 (SEQ ID NO: 1) has a relative molecular weight, as determined by SDS-PAGE, of about 20KDa. N-terminal amino acid sequencing of purified CSAP 20 (SEQ ID NO: 1) provided the amino acid sequence given in Table 1. A computer homology search conducted of the GENBANK data base revealed no protein sequences that share significant homology with the N-terminal sequence of CSAP 20 (SEQ ID NO: 1).

CSAP54 (SEQ ID NO: 2) has an apparent relative molecular weight, measured by SDS PAGE, of approximately 54KDa. Purified CSAP54 was subjected to N-terminal amino acid sequence analysis. The N-terminal amino acid sequence of CSAP54 (SEQ ID NO: 2) is provided in Table 2. A computer homology search against the GENBANK data base revealed significant homology between the N-terminal sequence of CSAP54 (SEQ ID NO: 2) and the beta chain of the H+ transporting ATP synthase from the photosynthetic bacterium Rhodopseudomonas blastica (GENBANK Accession number S04675; Tybulewicz et al., *J. Mol. Bio.* 179:185–214 (1984). The homology between the N-terminal amino acid sequence of CSAP54 (SEQ ID NO: 2) and the *R. blastica* protein can be seen in table 4.

The protein CSAP59 (SEQ ID NO: 3) has an approximate relative molecular weight of about 59 KDa, as measured by SDS-PAGE. Purified CSAP59 (SEQ ID NO: 3) has been subjected to N-terminal amino acid sequence analysis. The N-terminal amino acid sequence of CSAP59 (SEQ ID NO: 3) is provided in Table 3. The amino acid sequence in Table 3 was used in a computer search against the GENBANK data base. The search revealed significant homology between the N-terminal sequence of CSAP59 (SEQ ID NO: 3) and the alpha chain of H+transporting ATP synthase from the following organisms: the photosynthetic bacterium *Rhodospirillum rubrum*, (GENBANK Accession number S08581, Falk et al., *Biochem. J.* 228:391–407 (1985)), a Synechococcus species (GENBANK Accession number S10831, Cozens et al., *J. Mol. Bio.* 194:359–383 (1987)), an Anabaena species (GENBANK Accession number G31090, McCorn et al., *J. Bacteriol.* 194:3448–3458 (1988)) and from the chloroplast of *Marchantia polymorpha* (GENBANK Accession number A01021, submitted by Ohyama, K. (October 1986)). The homology between the N-terminal amino acid sequence of CSAP59 (SEQ ID NO:3) and the other proteins can be seen in table 5.

By use of the term "CSAP", it is intended not only proteins having the exact same amino acid sequence as Acetobacter CSAP20 (SEQ ID NO: 1), CSAP54 (SEQ ID NO: 3), and CSAP59 (SEQ ID NO: 3), but also CSAP derivatives capable of binding to bacterial cellulose synthase and/or having other CSAP biological activities. It will be appreciated that the term "CSAP" includes analogous proteins from species and strains of cellulose producing bacteria, other than the cellulose producing species of Acetobacter from which CSAP20 (SEQ ID NO: 1), CSAP54 (SEQ ID NO: 2), and CSAP59 (SEQ ID NO: 3) was initially isolated. These CSAP analogous proteins may have primary amino acid sequences that are either identical or homologous to, but somewhat different in primary amino acid sequence from CSAP proteins isolated herein.

The term CSAP derivative is defined to include polypeptides possessing CSAP biological activity and/or CSAP immunological activity. By CSAP immunological activity, it is intended that a polypeptide with CSAP immunological activity can specifically bind with antibodies specific for a given CSAP, or can, upon injection into animals (with suitable adjuvants), be used to induce an immune response specific for a given CSAP. Unless indicated otherwise, the term "CSAP derivative" means CSAP derivatives with biological activity and CSAP immunological activity. The term "CSAP biological activity" refers to various distinguishing features of CSAP proteins other than their immunological activity and structure (of course biological activity is a function of the structure of a protein). These distinguishing features are a consequence of the biological role that CSAP proteins play in a cell in which CSAP proteins are endogenous, for example, the biological activity of binding to cellulose synthase. CSAP20 (SEQ ID NO: 1), CSAP54 (SEQ ID NO: 2), and CSAP59 (SEQ ID NO: 3) have several biological activities, some of these biological activities are possessed by more than one of the CSAP proteins, for example, the ability to bind cellulose synthase. Although the full spectrum of CSAP biological activities has not presently been determined, some of the CSAP biological activities may be found by searching for homology between the amino sequence of CSAP proteins and proteins of known biological function, and subsequently seeking to identify the same or similar biological activities of homologous proteins in CSAP proteins.

Derivatives of CSAP proteins with CSAP biological activity typically have amino acid sequences that consist of the amino acid sequence of the naturally occurring CSAP proteins or the amino acid sequences of naturally occurring CSAP proteins with minor variations, including naturally occurring allelic variations. Derivatives of CSAP proteins may include polypeptides with the amino acid sequence of a given CSAP with one or more amino acid substitutions. Preferably, these amino acid substitutions are the result of the substitution of one amino acid with another amino acid having a similar structural and/or chemical properties, such as the replacement of a leucine with an isoleucine or valine, an aspartate with a glutamate, or a threonine with a serine, i.e., conservative amino acid replacements. Furthermore, CSAP derivatives may include polypeptides with the amino acid sequence of a naturally occurring CSAP, but possessing various minor amino acid deletions and/or insertions, typically in the range of about 1 to 5 amino acids, as well as one or more amino acid substitutions. Guidance in determining which CSAP amino acids may be replaced or deleted without abolishing CSAP biological activities of interest may be found by searching computer libraries of protein amino acid sequences for proteins that are homologous to a given CSAP and minimizing the number of amino acid sequence changes in regions of homology between a given CSAP and CSAP homologous proteins detected by a computer homology search. Additionally, CSAP amino acid residues that may be replaced or deleted without abolishing CSAP biological activities of interest may be determined by systematically making insertions, deletions, or replacement of CSAP amino acids (by recombinant DNA techniques) and assaying for the biological activities of interest.

Naturally occurring CSAP proteins, including CSAP20, CSAP54, and CSAP59, may be obtained by purifying cellulose synthase from cellulose synthase producing bacteria, Acetobacter xylinum being particularly preferred, by the cellulose entrapment method described in Mayer et al., *Proc. Natl. Acad. Sci. USA* 88:5472–5476. CSAP proteins co-purify with bacterial cellulose synthase. The CSAP proteins may be purified away from bacterial cellulose synthase using conventional separation techniques such as gel filtration chromatography, ion exchange chromatography, polyacrylamide gel electrophoresis, chromatofocusing, and the like.

The subject invention also provides for nucleotide sequences encoding CSAP20 (SEQ ID NO: 1), CSAP54 (SEQ ID NO: 2) and CSAP59 (SEQ ID NO: 3) and the primary amino acid sequences of these proteins. The genes encoding CSAP20 (SEQ ID NO: 1), CSAP54 (SEQ ID NO: 2) and CSAP59 (SEQ ID NO: 3) are referred to as csap20, csap54 and csap59, respectively. The primary amino acid sequences of these CSAP proteins may be determined by isolating genes encoding CSAP proteins and subjecting the isolated nucleotide sequences to conventional DNA sequencing procedures. The genes encoding the CSAP proteins may be conveniently isolated using conventional molecular cloning techniques based on, among other methods, hybridization of the N-terminal sequences of the CSAP protein of interest or antibodies to the CSAP protein of interest, e.g., corresponding to a portion of the N-terminal amino acid sequence. Techniques for cloning proteins based on this information are well-known to the person of average skill in the art of molecular biology. Among the numerous publications describing how to clone genes based on partial amino acid sequences or antibodies specific for the proteins are *Molecular Cloning: A Laboratory Manual*, 2nd Edition, Sambrook, et al., Cold Spring Harbor Laboratory Press, Cold Spring Harbor, N.Y. (1989) and *Guide to Molecular Cloning Techniques: Methods and Enzymology, Vol. 152*, Berger and Kimmel, Academic Press, San Diego, Calif. (1987). Typically, genetic libraries will be prepared from the Acetobacter genome, or the genome of other cellulose producing microorganisms. The gene library may then be screened using antibodies specific to the protein of interest or oligonucleotide probes derived from amino acid sequence information obtained by sequencing the protein of interest. Additional methods of isolating genes encoding CSAP proteins include complementation of mutations in bacteria naturally encoding CSAP proteins, such as *Acetobacter xylinum*. Additionally, CSAP proteins encoding nucleotide sequences may be isolated, at least in part, without relying on the formation of genetic libraries by employing PCR (polymerase chain reaction) involving primer oligonucleotides specific for the CSAP gene of interest.

The nucleotide sequences of isolated CSAP encoding genes may be determined using conventional DNA sequencing technology, including the Sanger dideoxy method, the Maxam and Gilbert chemical cleavage method, and the like. By analyzing the nucleotide sequence of CSAP encoding genes, the primary amino acid sequence of the various CSAP proteins may be readily determined.

In addition to providing for nucleotide sequences with the sequence of naturally occurring CSAP encoding genes, the subject invention also provides for numerous nucleotide sequences bearing homology to the nucleotide sequence of naturally occurring CSAP encoding genes. Sequences of interest include nucleotide sequences encoding CSAP proteins and CSAP protein derivatives.

It will be appreciated by those skilled in the art that as a result of the degeneracy of the genetic code, a multitude of nucleotide sequences, some bearing minimal nucleotide sequence homology to the nucleotide sequence genes naturally encoding CSAP proteins may be produced. The invention has specifically contemplated each and every possible variation of peptide or nucleotide sequence that could be made by selecting combinations based on the possible amino acid and codon choices made in accordance with the standard triplet genetic code as applied to the nucleotide sequence of naturally occurring CSAP encoding genes and all such variations are to be considered as being specifically disclosed.

Although nucleotide sequences encoding CSAP proteins and CSAP protein derivatives are preferably capable of hybridizing to the nucleotide sequence of naturally occurring CSAP genes under stringent conditions, it may be advantageous to produce nucleotide sequences encoding CSAP proteins or CSAP protein derivatives, possessing substantially different coding sequences. Codons can be selected for use in a particular expression host organism in accordance with the frequency with which a particular codon is utilized by the host, if desired, to increase the rate at which expression of the peptide occurs. Other reasons for substantially altering the nucleotide sequence encoding a CSAP protein and/or a CSAP protein derivative without altering the amino acid sequence include the production of RNA transcripts having more desirable properties, e.g., greater half-life, than transcripts produced from the natural CSAP, and the like.

Nucleotide sequences encoding CSAP proteins and CSAP protein derivatives may be joined to a variety of other nucleotide sequences of interest by means of well established recombinant DNA techniques (see, for example, Sambrook, et al., *Molecular Cloning: A Laboratory Manual, 2nd Ed.*, Cold Spring Harbor (1989).

Nucleotide sequences of interest for joining include an assortment of vectors, e.g., plasmids, cosmids, λ phage derivatives, phasmids, and the like, that are in the public domain. Vectors of interest include expression vectors, replication vectors, probe generation vectors, sequencing vectors, and the like. In general vectors of interest, may contain an origin of replication functional in at least one organism, convenient restriction endonuclease digestion sites, and selectable markers for the host cell.

Isolated CSAP encoding genes, including csap20, csap54, and csap59 may be used to genetically manipulate cellulose providing bacteria so as to modulate the amount and/or quality of cellulose produced under specific growth conditions. For example, isolated CSAP encoding genes may be used to inactivate endogenous CSAP genes, add new promoters to endogenous CSAP genes, and add multiple plasmid borne copies of CSAP genes. General techniques for the genetic manipulation of bacteria can be found in *Methods in Enzymology Volume 204*, Academic Press, San Diego, Calif. (1992). Specific techniques for the genetic manipulation of cellulose producing Acetobacter species can be found in PCT patent publication WO90/12098.

Nucleotide sequences encoding CSAP proteins may be used to produce CSAP proteins using well-known methods of recombinant DNA technology. Among the many publications teaching methods for the expression of genes after they have been isolated is *Gene Expression Technology, Methods and Enzymology, Vol. 185*, edited by Goeddel, Academic Press, San Diego, Calif. (1990). CSAP proteins may be expressed in a variety of host cells, either prokaryotic or eukaryotic. Host cells may be from species the same or different than species from which the CSAP encoding sequences are naturally present, i.e., endogenous. Advantages of producing the CSAP proteins by recombinant DNA technology include obtaining highly enriched sources of the proteins for purification and the availability of simplified purification procedures.

Another aspect of the subject invention is to provide for nucleic acid hybridization probes. Such probes may be used to isolate CSAP genes and/or CSAP homologous genes from genetic libraries prepared from a variety of cells, in particular the cells of cellulose producing bacteria. Furthermore, nucleic acid hybridization probes may be used to detect the transcription of CSAP or CSAP homologous genes from a variety of organisms by means of northern blots, in situ hybridizations, and the like. Suitable nucleic acid hybridization probes for the detection of CSAP and CSAP homologous sequences comprise at least 14, preferably 25, and more preferably at least 50% of the nucleotides, from the sequence of a given CSAP gene. Hybridization probes may be labeled by a variety of labels including radionuclides, such as $^{32}P$ or $^{35}S$, or enzymatic labels such as alkaline phosphatase coupled to the probe via avidin/biotin coupling systems or the like.

An additional use for nucleic acid hybridization probes involves their use as primers for PCR, the polymerase chain reaction. The polymerase chain reaction is described in detail in U.S. Pat. Nos. 4,965,188 and 4,683,202 and 4,800,195.

Probes for hybridization may be synthesized by both enzymatic, and in vitro techniques. Short hybridization probes are preferably synthesized by in vitro methodology such as the use of commercially available DNA synthesizers such as machines sold by Applied Biosystems.

For example, nucleotide sequences of lengths greater than 10 base pairs may be produced by commercially available machines. Oligonucleotides produced by in vitro synthesis may be readily spliced together using generally known recombinant DNA techniques.

Other means of producing CSAP hybridization probes include the cloning of nucleic acid sequences encoding CSAP and CSAP derivatives into vectors for the production of RNA probes. Such vectors are known in the art and are commercially available, and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding CSAP or CSAP derivatives entirely by synthetic chemistry, after which the gene can be inserted into any of the many available DNA vectors using reagents, vectors and cells that are freely available and in the public domain at the time of the filing of this application. Synthetic chemistry may be used to reproduce the entire sequence of a CSAP encoding gene, any portion thereof, or to introduce mutations into the sequence.

Antibodies specific for a given CSAP may be produced by using CSAPs, or derivatives thereof, for the induction of said CSAP-specific antibodies. By induction of antibodies, the intent is not only the stimulation of an immune response by injection into animals, but analogous steps in the production of synthetic antibodies such as the screening of recombinant immunoglobulin libraries, Orlandi et al., *PNAS USA* 86: 3833–3837 (1989) or Huse et al., i Science 256: 1275–1281 (1989), or the in vitro stimulation of lymphocyte populations. Also of interest is the development of antibody preparations, including monoclonal antibodies, specific for single epitopes on CSAPs, i.e., monospecific antibodies.

CSAP derivatives for use in the induction of antibodies of interest do not need to have biological activity; however, CSAP derivatives for use in the induction of antibodies will necessarily have immunological activity. Polypeptides for use in the induction of CSAP-specific antibodies may have an amino acid sequence consisting of at least five amino acids preferably at least 10 amino acids, mimicking a portion of the amino acid sequence of CSAP and may contain the entire amino acid sequence of a CSAP.

Short oligopeptides, i.e., containing about 20 amino acids or less, are of particular interest for both the induction and the screening of mono-specific antibodies specific for epitopes of interest. In general, oligopeptides for use in the induction of epitope specific monospecific antibodies will have an amino acid sequence corresponding to at least a portion of the epitope of interest.

Current technology, e.g., Winter and Milstein, Nature, 349:293–299 (1991), provides for a number of highly specific binding reagents based on the principles of antibody formation.

In a preferred embodiment of the subject invention, CSAP and CSAP derivative specific binding reagents and/or antibodies are produced by the injection of CSAP and/or CSAP derivatives with immunological activity into mammals for the production of antisera or the production of hybridoma fusion partners. CSAP and/or CSAP derivatives for the induction of antibody response are preferably injected into mammals in conjunction with the presence of various adjuvants such as Freund's complete adjuvant, and the like, in order to maximize the immune response to CSAP and/or CSAP derivatives. More detailed descriptions of the methodology for the production of antibodies can be found in generally available publications such as Harlow and Lane, *Antibodies: A Laboratory Manual*, Coldspring Harbor Press, Coldspring Harbor, N.Y. (1988).

Salts of any of the macromolecules described herein will naturally occur when such molecules are present in (or isolated from) aqueous solutions of various pHs. All salts of peptides and other macromolecules having the indicated biological activity are considered to be within the scope of the present invention. Examples include alkali, alkaline earth, and other metal salts of carboxylic acid residues, acid addition salts (e.g., HCl) of amino residues, and zwitterions formed by reactions between carboxylic acid and amino residues within the same molecule.

Although CSAP20 (SEQ ID NO: 1), CSAP54 (SEQ ID NO: 2) and CSAP59 (SEQ ID NO: 3) have biological functions that are not explicitly disclosed in the present application, it will be apparent to those skilled in the art of molecular biology that the CSAP proteins have numerous uses based on their ability to associate with cellulose synthase, a protein of well recognized utility in the production of cellulose. Uses for the CSAP proteins include the purification of cellulose synthase. Affinity chromatography columns containing one or more CSAP proteins or antibodies to CSAP proteins may be used to purify cellulose synthase based on the affinity of cellulose synthase for the CSAP protein or the affinity of the CSAP specific antibody for a portion of a cellulose synthase complex. Similarly, CSAP and CSAP derivatives may be used to generate CSAP specific antibodies capable of detecting the cellulose synthase complex and/or CSAP proteins. These CSAP specific antibodies that detect the cellulose synthase complex and/or CSAP proteins may be used in conventional immunoassays, such as ELISA, RIA and western blots, to detect cellulose synthase complex. Similarly, the ability of CSAP proteins to specifically associate with bacterial cellulose synthase permits CSAP proteins to be used in place of cellulose synthase specific antibodies in immunoassays for cellulose synthase.

The following examples are offered for the purpose of illustrating, not limiting, the subject invention.

EXAMPLES

Discovery of CSAP Proteins

A cellulose product enzyme entrapped preparation was produced according to the product entrapment procedure essentially as described in Mayer et al., *Proc. Natl. Acad. Sci. USA* 88:5472–5476. The sample was separated by a modified version of the Laemmli procedure modified as follows:

(1) Sample buffer contained: 0.1M sucrose; 3% SDS; 62 mM Tris pH 6.9; 2 mM EDTA; 130 mM beta-mercapto-ethanol and bromophenol blue.

(2) Mixtures of enzyme in sample buffer were incubated for 15 minutes at 37° C. (instead of the typical 2 minutes at 100° C.), prior to separation by SDS-PAGE.

(3) Stacking gels and running buffer contained thioglycolic acid (0.75 μl/100 ml).

Bands of 20, 54, 59, 67, 83 and 90 kD were detected after staining.

N-Terminal Analysis

Using the above procedures, gels were prepared separating the cellulose synthase complex. The gels were subsequently blotted onto PVDF membranes using a semi-dry blotter at 0.9mA/cm² for three hours. The membrane was stained for five minutes in a solution of 0,025%, Coomassie blue in 40% methanol partially destained with a 50% methanol. Bands were excised according to molecular weight. The excised bands were subjected to an N-terminal amino acid sequence analysis. N-terminal amino acid sequence analysis of the 67, 83, and 90 kD bands revealed that the bands were formed by the gene products of the bcsB, bcsA, and bcsB genes of the bacterial cellulose synthase operon, respectively (data not included). The amino acid residue sequences obtained for the 20 kD, 54 kD and 59 kD bands are provided in Tables 1, 2 and 3, respectively, in single letter amino acid code. In Tables 1–3, the amino acids marked by parentheses indicate that a weak peak was obtained during sequencing; question marks indicate that the identity of the amino acid residue could not be ascertained; positions with more than one amino acid residue indicated that multiple peaks were obtained (as for each of the indicated residues); and plus marks indicate that of the multiple peaks found at a given sequencing cycle, the plus marked residue peak was the highest.

TABLE 1

N-terminal amino acid sequence of CSAP20 (SEQ ID NO: 1)

| 1 | 2 | 3 | 4 | 5 | 6 | 7 | 8 | 9 | 10 | 11 |
|---|---|---|---|---|---|---|---|---|----|----|
| T | T | I | T | G | P | Y | V | D | I  | G  |
| 12 | 13 | 14 | 15 | 16 | 17 | 18 | 19 | 20 | 21 | 22 |
| G | G | Y | N | L | T | Q | T | Q | H | M |
| 23 | 24 | 25 | 26 | 27 | 28 | | | | | |
| P | R | A | G | G | (D) | | | | | |
| | | | | | (G) | | | | | |

TABLE 2

N-terminal amino acid sequence of CSAP54 (SEQ. ID NO: 3)

| 1 | 2 | 3 | 4 | 5 | 6 | 7 | 8 | 9 | 10 | 11 |
|---|---|---|---|---|---|---|---|---|----|----|
| S | N | V | V | ? | T | V | T | Q | V | ? |
| | | | | | P | | | | | |
| 12 | 13 | 14 | 15 | 16 | 17 | 18 | 19 | 20 | 21 | 22 |
| G | A | V | V | S | V | Q | F | H | ? | T |
| | | | | (D) | L | | | | | |
| 23 | 24 | | | | | | | | | |
| (A) | (P) | | | | | | | | | |

TABLE 3

N-terminal amino acid sequence of CSAP59 (SEQ. ID NO: 3)

| | 2 | 3 | 94 | 5 | 6 | 7 | 8 | 9 | 10 | 11 |
|---|---|---|----|---|---|---|---|---|----|----|
| M | E | I | (R) | P | S | E | I | S | (D) | I |
| S+ | | | | | | | | | | A |
| N | | | | | | | | | | |
| 12 | 13 | 14 | 15 | 16 | 17 | 18 | 19 | 20 | 21 | 22 |
| L | K | Q | Q | I | A | T | F | (D) | I | A |
| | | | | | | L | | | | |
| 23 | 24 | 25 | | | | | | | | |
| A | ? | T | | | | | | | | |
| | | V | | | | | | | | |

TABLE 4

CSAP54 Homology

```
CSAP54 1    .....SNVVXTVTQVXGAVVS VQFH........................ 20
                 ||||  |||  |||
S04675 1    MTMATTVSKGKVTQVI GAVVDVQFEGVLPAILNALETTNNGKKLILEVAQ 50
```

TABLE 5

CSAP59 Homology

```
                10          20
CSAP59    SEIRP S EISDILKQQIATLFDIAAXTV
          |||: : |||: |||: |||: :
S08581    MEIRAAEISAILKEQIANFGTEAESAEVGQVLSVGDGIARVYGLDNVQAGEMVEFANGVK
                10          20          30          40          50          60
```

TABLE 5-continued
CSAP59 Homology

```
               10         20
CSAP59    SEIRPS EISDILKQQI ATLFDI AAXTV
          || |:  | ||: |: :  | | |
S10831    MVSIRPDEISS II RQQIEQYSQDVKVENVGTVLQVGDGIARIYGLQQVMSGELVEFEDGT
               10         20         30         40         50         60

CSAP59    SEIRPS EISDILKQQI ATLFDIAAXTV
          || |:  | ||: |: :  | | |
G31090    MSIS IRPDEISS II QQQIEQYDQEVKVANVGTVLQVGDGIARIYGLEKAMAGELLEFEDG
               10         20         30         40         50         60

CSAP59    S EIRPS EISDILKQQI ATLFDIAAXTV
          :  || |:  | ||: |: :  | |
A01021    MVNIRPDEISS II RKQIEQYNQEVKIVNIGTVLQVGDGIARIYGLDKVMAGELVEFEDGT
               10         20         30         40         50         60
```

EQUIVALENTS

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The foregoing written specification is considered to be sufficient to enable one skilled in the art to practice the invention. Indeed, various modifications of the above-described modes for carrying out the invention which are obvious to those skilled in the field of molecular biology or related fields are intended to be within the scope of the following claims.

What is claimed is:

1. A purified Cellulose synthase Associated Protein isolated from an Acetobacter organism.

2. A purified protein according to claim 1, wherein the Acetobacter is Acetobacter 1306-21.

3. A purified protein according to claim 1, wherein the protein is in Cellulose Synthase Associated Protein 20 and comprises the amino acid sequence of SEQ ID NO: 1.

4. A purified protein according to claim 1, wherein the protein is in Cellulose Synthase Associated Protein 54 and comprises the amino acid sequence of SEQ ID NO: 2.

5. A purified protein according to claim 1, wherein the protein is in Cellulose Synthase Associated Protein 59 and comprises the amino acid sequence of SEQ ID NO: 3.

* * * * *

UNITED STATES PATENT AND TRADEMARK OFFICE
CERTIFICATE OF CORRECTION

PATENT NO. : 5,382,656

DATED : January 17, 1995

INVENTOR(S) : Benziman, et al.

It is certified that error appears in the above-identified patent and that said Letters Patent is hereby corrected as shown below:

Column 9, line 39 replace "0,025%," with --0.025%,--;

Column 10, replace Table 3 with the following table:

UNITED STATES PATENT AND TRADEMARK OFFICE
CERTIFICATE OF CORRECTION

PATENT NO. : 5,382,656
DATED : January 17, 1995
INVENTOR(S) : Moshe Benziman, et al It is certified that error appears in the above-indentified patent and that said Letters Patent is hereby corrected as shown below:

TABLE 3

N-terminal amino acid sequence of CSAP59 (SEQ. ID NO:3)

| 1 | 2 | 3 | 4 | 5 | 6 | 7 | 8 | 9 | 10 | 11 |
|---|---|---|---|---|---|---|---|---|----|----|
| M | E | I | -(R) | P | S | E | I | S | (D) | I |
| S+ |   |   |     |   |   |   |   |   |     | A |
| N |   |   |     |   |   |   |   |   |     |   |

| 12 | 13 | 14 | 15 | 16 | 17 | 18 | 19 | 20 | 21 | 22 |
|----|----|----|----|----|----|----|----|----|----|----|
| L  | K  | Q  | Q  | I  | A  | T  | F  | (D)| I  | A  |
|    |    |    |    |    | L  |    |    |    |    |    |

| 23 | 24 | 25 |
|----|----|----|
| A  | ?  | T  |
|    |    | V  |

Signed and Sealed this

Nineteenth Day of September, 1995

Attest:

BRUCE LEHMAN

Attesting Officer     *Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH:28
        ( B ) TYPE: amino acid
        ( D ) TOPOLOGY: linear ( i i ) MOLECULE TYPE: protein ( i x ) SEQUENCE DESCRIPTION: SEQ ID NO:1:

```
Thr  Thr  Ile  Thr  Gly  Pro  Tyr  Val  Asp  Ile  Gly  Gly
1                   5                        10

Gly  Tyr  Asn  Leu  Thr  Gln  Thr  Gln  His  Met  Pro  Arg
          15                      20

Ala  Gly  Gly  Asp
25
```

( 2 ) INFORMATION FOR SEQ ID NO:2:

( i ) SEQUENCE CHARACTERISTICS:
        ( A ) LENGTH: 24
        ( B ) TYPE: amino acid
        ( D ) TOPOLOGY: linear ( i i ) MOLECULE TYPE: protein ( i x ) SEQUENCE DESCRIPTION: SEQ ID NO:2:

```
Ser  Asn  Val  Val  Xaa  Tyr  Val  Tyr  Gln  Val  Xaa  Gly
1                   5                        10

Ala  Val  Val  Ser  Val  Gln  Phe  His  Xaa  Tyr  Ala  Pro
          15                      20
```

( 2 ) INFORMATION FOR SEQ ID NO:3:

( i ) SEQUENCE CHARACTERISTICS:
        ( A ) LENGTH: 25

(B) TYPE: amino acid
(D) TOPOLOGY: linear (ii) MOLECULE TYPE: protein (ix) SEQUENCE DESCRIPTION: SEQ ID NO:3:

```
Met Glu Ile Arg Pro Ser Glu Ile Ser Asp Ile Leu
1               5                   10
Lys Gln Gln Ile Ala Thr Phe Asp Ile Ala Ala Xaa
        15                  20
Thr
25
```